United States Patent [19]

Utterberg

[11] Patent Number: 5,360,395
[45] Date of Patent: Nov. 1, 1994

[54] PUMP CONDUIT SEGMENT HAVING CONNECTED, PARALLEL BRANCH LINE

[76] Inventor: David S. Utterberg, 1080 Chestnut St., San Francisco, Calif. 94109

[21] Appl. No.: 170,534

[22] Filed: Dec. 20, 1993

[51] Int. Cl.$^5$ .............................................. A61B 1/00
[52] U.S. Cl. ........................................ 604/4; 604/83; 604/283; 604/905
[58] Field of Search ................... 604/4, 5, 83, 283, 905

[56] References Cited

U.S. PATENT DOCUMENTS

| | | | |
|---|---|---|---|
| 4,037,599 | 7/1977 | Raulerson | 604/4 |
| 4,204,525 | 5/1980 | Olson | 604/83 |
| 4,280,496 | 7/1981 | Van Baelen | 604/83 |
| 4,416,280 | 11/1983 | Carpenter et al. | 604/83 |
| 5,061,365 | 10/1991 | Utterberg | |

OTHER PUBLICATIONS

Publication from the Drake-Willock Company—Drake-Willock 7000 or 7200—one page.
Publication from the Medisystems Corporation—Medisystems D3-4361/9711—ReadySet Blood-tubing for Cobe Centry II, Baxter SPS (Single Needle) and Althin System 1000—one page.

*Primary Examiner*—Jerome L. Kruter
*Attorney, Agent, or Firm*—Gerstman, Ellis & McMillin

[57] ABSTRACT

A set for conveying blood between a patient and blood treatment apparatus such as a dialyzer. The set comprises a blood flow conduit, connecting with a patient's vascular system, and means for connecting the conduit with the dialyzer. A portion of the conduit comprises an enlarged-diameter, tubular pump segment connected at each pump segment end with a connector. The connectors also are each connected in substantially straight-line relation to other portions of the blood flow conduit. Typically, both connectors also each connect to a branch line in a relation substantially parallel to the connection of the other blood flow conduit portion and the connected tubular pump segment. Thus, the set is more capable of being rolled up and packaged in an automated manner, since it can be free of branching connections which connect at a substantial angle to the overall axis of the set.

15 Claims, 1 Drawing Sheet

PUMP CONDUIT SEGMENT HAVING CONNECTED, PARALLEL BRANCH LINE

BACKGROUND OF THE INVENTION

Arterial sets for hemodialysis are known to conventionally carry a blood flow tubing between a connector for the arterial fistula of the patient at one end of the set and a connector to the dialyzer at the other end of the set. Between the set ends, an enlarged-diameter pump tube segment is provided, being tubing which fits into the track of a roller pump for rolling compression by the rollers of the pump. This provides the necessary pressure to circulate the blood at a desired flow rate through the entire system from the patient, through the dialyzer, and back to the patient.

Additionally, both arterial and venous dialysis sets typically carry a so-called "drip chamber", although at current blood flows through dialyzers, the volume of blood passing through the set is much greater than that represented by a "drip".

Hemodialysis is a relatively expensive medical procedure, since it is typically performed about three times a week on a continuing basis through the remaining life of the patient, or at least until a kidney transplant is obtained. Thus, there is significant need to reduce the cost of dialysis, which of course includes the cost of the blood sets used, and are typically disposed of after one use. Even a relatively small cost reduction in the manufacture of blood sets for dialysis can result in significant cost savings, because of the large numbers of such blood sets that are used.

At the present time, blood sets for dialysis which carry a pump segment substantially all have such pump segments that terminate in branching connectors. The branching connectors also receive the ends of the other portions of the blood flow conduit of the set, with such flow conduit portions being generally of less outer diameter than the pump segment. Also, each of the connectors at opposite ends of the pump segment typically carry a branch line which connects with the pump segment at a 90° angle. One of these branch lines is for connection to a set for saline solution supply, while the other of the branch lines typically connects to a source of heparin.

Pump sets are typically packaged in a rolled-up manner of substantially circular appearance, so that the package may be compact and neat. However, because of the presence of the perpendicular branch lines, the rolling of the set into a circular array for packaging is not easily done in an automated manner, but rather must be accomplished substantially by hand. This of course adds to the cost of packaging of the set, which adds to the overall set cost.

In addition, this 90 degree branch attachment results in complicated set-up, twisted lines, and the like by the following action: The orientation of the inlet 90 degree branch can by manipulated by the healthcare worker when the pump segment connector is attached to the first end of the U-shaped pump housing. For example, the inlet end pump segment connector can be oriented so the 90 degree branch can be pointed outwardly, parallel to the face plate of the machine. This facilitates easy attachment of the branch (IV) line to the typical line that connects at the inlet end of the pump tubing saline source.

However, the outlet 90 degree branch attachment cannot be so easily manipulated because its orientation is determined by the pronation (twisting) of the pump segment, being rotated in its U-shape by the pump rollers. Thus, while it is desirable for the outlet 90 degree branch attachment to be pointed outwardly, parallel to the face of the machine (for attachment to the heparin syringe pump), it ends up in a random location, pointing to the right, left, forward or back towards the face plate.

This leads to difficult set-up and even kinks in this attachment line as it must be redirected. Finally, the pump segment tends to continue to pronate during the procedure through the continued rotation of the pump rollers. The 90 degree attachment and connected line thus gets further twisted.

By this invention, a set for conveying blood between a patient and a hemodialyzer (or another blood treatment apparatus) is provided, in which the set is significantly more capable of automated rolling into a circular array, so that the sets may be packaged in a more automated packaging process than the sets of the prior art. The set of this invention may be automatically rolled, installed in a package, and sealed therein without being touched by human hands. Thus, the set of this invention may exhibit a reduced overall cost, when compared with prior art sets which are otherwise comparable. Also, by this invention a set is provided in which the set up of the pump segment attachment lines is more convenient and less likely to kink.

DESCRIPTION OF THE INVENTION

In accordance with this invention, a set for conveying blood between a patient and blood treatment apparatus is provided which comprises a blood flow conduit means for connecting the conduit with a patient's vascular system and means for connecting the conduit with the blood treatment apparatus. A portion of the conduit of the set comprises a tubular pump segment which is connected at least at one pump segment end with a connector. The above connector or connectors also each connect in substantially straight-line relation to other portions of the blood flow conduit.

At least one of the connectors also connects to a branch line in a relation which is substantially parallel to the connection of the connected other portion of the blood flow conduit (and may also be generally parallel to the connection of the pump segment). Typically, both of the connectors at opposed ends of the pump segment each carry the substantially parallel branch line connection with a branch conduit.

By this means, the set of this invention is more capable of being rolled up and packaged in an automated manner than corresponding prior art sets. Specifically, the rolled-up set will be free of tubular members which project inwardly from the circular set in generally radial manner, so that the space within the rolled-up set is essentially free of set components.

Also, by this means the branch conduits may be shorter. Because pronation of the pump segment connector does not orient the conduit in the wrong direction, the branch conduits can be shorter, while still being capable to mate distally with a machine mounted connector, for example a heparin line conduit connecting to a syringe may mate with the connector of this invention. Also, set up is easier, and kinks are less likely.

The tubular pump segment is typically of greater diameter than the other portions of the blood flow conduit adjacent the connectors, with the exception of course of a drip chamber and the like, which is typically present. Also, the branch line or lines present which connect with the connectors at the ends of the pump segment are typically of less diameter than the other portions of the blood flow conduit adjacent the connectors. Specifically, it is preferred for the set of this invention to have a pump segment of an outer diameter of 8.5 to 12.5 millimeters; a blood flow conduit adjacent the connectors having an outer diameter of about 4.5 to 7.5 millimeters; and the branch line or branch lines having an outer diameter of about 1.6 to 4.0 millimeters. Some sets of the prior art have tubing diameters similar to the above.

Thus, a set for hemodialysis or the like is provided in which the functioning is equivalent to or better than that of prior art sets, but the set may be rolled by automated means into a circular array without inconvenient, inwardly extending branching sets from the circular array toward the origin of the circle, which facilitates automated packaging of the set of this invention and eliminates branch conduit kinking and permits a reduction in the length of branch lines.

DESCRIPTION OF SPECIFIC EMBODIMENTS

Figure 1:
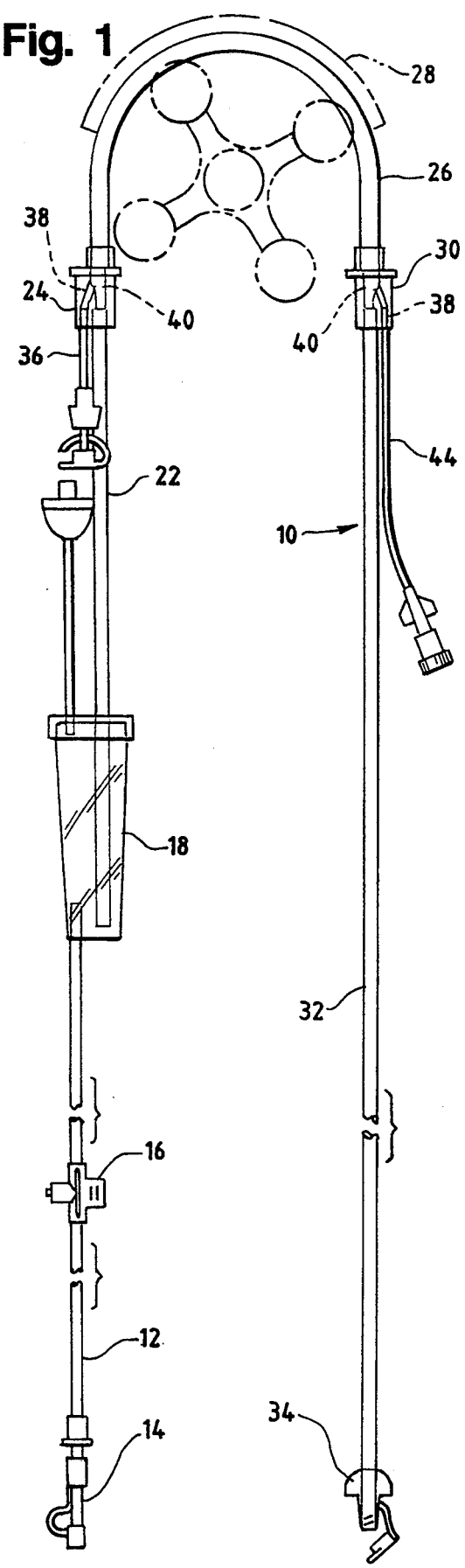
FIG. 1 is an elevational view of the set of this invention, shown mounted in a roller pump.

Referring to the drawings, arterial set 10 for hemodialysis is shown, comprising a proximal length of blood tubing 12 terminating in a connector 14 for connection with a patient's fistula through a needle.

Tubing 12 carries a conventional injection site 16, and communicates with a conventional blood chamber 18. Blood chamber 18 carries a pressure monitor line 20, as well as a second length of blood flow conduit 22.

Blood flow conduit 22 communicates through a three conduit connector 24 with a length of roller pump tubing 26, which is shown to be mounted in a roller pump system 28, illustrated in broken lines.

A second, three conduit connector 30 terminates the other end of roller pump tubing, and connects with a third length of blood flow conduit 32. The other end of blood flow conduit 32 is terminated with a connector 34 for a hemodialyzer.

The particular dialysis set shown is a set for use in the "pre-pump" mode. However, the invention of this application may be used for dialysis sets in the post-pump mode as well and elsewhere.

In accordance with this invention, each of connectors 24, 30 provide connection for three separate conduits. In the case of connector 24, connection is provided for blood conduit 22, pump segment 26, and a third conduit 36, which may be used for connection with a source of saline solution or anticoagulant solution. In corresponding sets of the prior art, the saline line analogous to line 36 joins the remainder of the set in a perpendicular direction through a connector analogous to connector 24.

Figure 3:
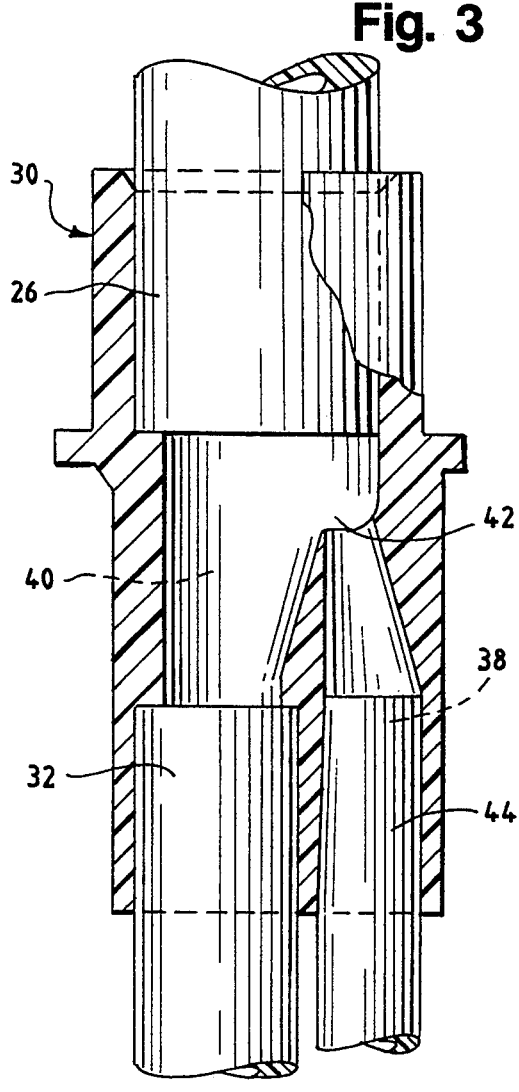
FIG. 3 is an enlarged elevational view, taken partly in vertical section, of one of the connectors of the set of FIG. 1.

In accordance with this invention, connector 24 is provided with a pair of lumens 38, 40, which are in generally longitudinal relation to each other, and which join at one end thereof 42 as shown in FIG. 3 (although FIG. 3 is an enlarged view of connector 30, which is in reversed position but otherwise is of identical structure to connector 24).

With respect to connector 30, it provides connection between an end of pump segment 26 and blood tube 32, also providing connection with a branch conduit 44, with the connection between the conduits being in longitudinal rather than transverse relation as shown. Branch conduit 44 may connect with a source of heparin, and is held in connector lumen 38. Pump segment 26 and blood tube 32 are held in opposite end portions of lumen 40.

The respective tubes are sealed in the connectors in conventional manner.

Figure 2:
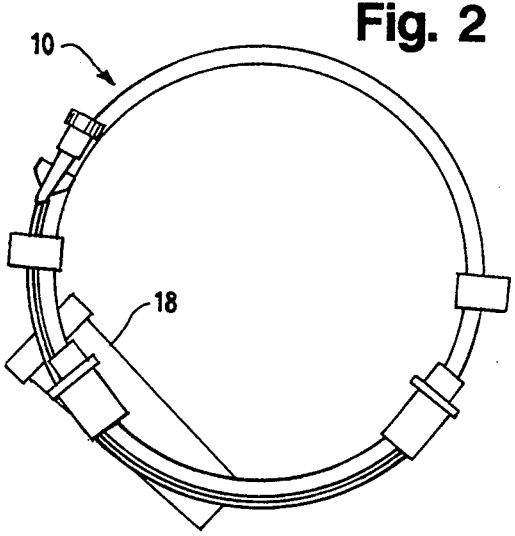
FIG. 2 is a plan view of the set of FIG. 1, shown in its rolled, packaged configuration prior to unwinding and use.

Because of the modification of this invention, it becomes substantially easier to wrap set 10 into a generally circular array as illustrated in FIG. 2, using automated equipment if desired, thus providing further cost-reducing automation of the manufacturing process of set 10. Nevertheless, the respective longitudinal mounting of branch lines 36, 44 does not interfere with the use of the set, so that a dialysis set is provided which is fully competitive in its advantages and features with those of the prior art, but which can be manufactured with a higher degree of automation for significant cost reduction.

It is preferred for pump segment 26 to have an outer diameter of 8.5 to 12.5 mm, while blood flow conduits 12, 32 have an outer diameter of 4.5 to 7.5 mm. The branch lines 36, 44 may preferably have an outer diameter of 1.6 to 4.0 mm. Connectors 24, 30 may be made by injection molding, being proportioned in their respective longitudinal lumens 38, 40 to receive the respective tubular conduits of desired size as described above.

The above has been offered for illustrative purposes only, and is not intended to limit the scope of the invention of this application, which is as defined in the claims below.

That which is claimed is:

1. A set for conveying blood between a patient and blood treatment apparatus, which comprises:

a blood flow conduit; means for connecting the conduit with a patient's vascular system; means for connecting the conduit with the blood treatment apparatus; a portion of said conduit comprising an enlarged-diameter, tubular pump segment connected at each pump segment end with a connector, said connectors also each connecting in substantially parallel, straight-line relation to other portions of said blood flow conduit, at least one of said connectors also connecting to a branch line in a longitudinal relation to the connected other portion of the blood flow conduit, wherein said set is more capable of being rolled up and packaged in an automated manner than sets having acutely angled or perpendicular connections.

2. The set of claim 1 in which both of said connectors carry said longitudinally connected branch lines.

3. The set of claim 1 in which said tubular pump segment is of greater diameter than said other portions of said blood flow conduit adjacent said connectors, and said branch line is of less diameter than said other portions of said blood flow conduit adjacent said connectors.

4. The set of claim 3 in which said pump segment has an outer diameter of 8.5 to 12.5 mm.

5. The set of claim 3 in which said blood flow conduit adjacent said connectors has an outer diameter of 4.5 to 7.5 mm.

6. The set of claim 3 in which said branch line has an outer diameter of 1.6 to 4.0 mm.

7. The set of claim 3 in which said pump segment has an outer diameter of 8.5 to 12.5 mm.; and the blood flow conduit adjacent the connectors has an outer diameter of 4.5 to 7.5 mm.

8. The set of claim 7 in which said branch line has an outer diameter of 1.6 to 4.0 mm.

9. A set for conveying blood between a patient and a blood dialyzer, which comprises:

a blood flow conduit; means for connecting the conduit with a patient's vascular system; means for connecting the conduit with a blood flow path within the dialyzer; a portion of said conduit comprising an enlarged-diameter tubular pump segment connected at each pump segment end with a branching connector, said branching connectors also each connecting in substantially parallel, straight-line relation to other portions of said blood flow conduit, said connectors also each connecting to a branch line in a relation substantially parallel to the connection of the connected other portion of the blood flow conduit, said tubular pump segment having an outer diameter of 8.5 to 12.5 mm. and being of greater diameter than said other portions of said blood flow conduit adjacent said connectors, said other portions adjacent said connectors having an outer diameter of 4.5 to 7.5 mm., said branch lines each having an outer diameter of 1.6 to 4.0 mm., wherein said set is more capable of being rolled up and packaged in an automated manner than sets having acutely angled or perpendicular connections.

10. A set for conveying blood between a patient and blood treatment apparatus, which comprises: a blood flow conduit; means for connecting the conduit with a patient's vascular system; means for connecting the conduit with the blood treatment apparatus; a portion of the conduit comprising a tubular pump segment connected at each pump segment end with a connector, said connectors also each connecting in substantially parallel straight-line relation to other portions of said blood flow conduit, at least one of said connectors also connecting to a branch line in a relation substantially parallel to the connection of the connected other portion of the blood flow conduit, said set being rolled up into circular array free of set components extending substantially inwardly from said circular array.

11. The set of claim 10 in which both of said connectors carry said longitudinally connected branch lines.

12. The set of claim 11 in which said tubular pump segment is of greater diameter than said other portions of said blood flow conduit adjacent said connectors, and said branch line is of less diameter than said other portions of said blood flow conduit adjacent said connectors.

13. The set of claim 12 in which said pump segment has an outer diameter of 8.5 to 12.5 mm.

14. The set of claim 13 in which said blood flow conduit adjacent said connectors has an outer diameter of 4.5 to 7.5 mm.

15. The set of claim 14 in which said branch line has an outer diameter of 1.6 to 4.0 mm.

* * * * *